United States Patent
Dubovoy et al.

(10) Patent No.: US 11,918,667 B2
(45) Date of Patent: *Mar. 5, 2024

(54) ZIRCONIUM-BASED CLUSTER AS AN ANTIPERSPIRANT AND DEODORANT ACTIVE

(71) Applicant: Colgate-Palmolive Company, New York, NY (US)

(72) Inventors: Viktor Dubovoy, Cresskill, NJ (US); Long Pan, Somerset, NJ (US); Ravi Subramanyam, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 128 days.

This patent is subject to a terminal disclaimer.

(21) Appl. No.: 16/771,945

(22) PCT Filed: Dec. 10, 2018

(86) PCT No.: PCT/US2018/064756
§ 371 (c)(1),
(2) Date: Jun. 11, 2020

(87) PCT Pub. No.: WO2019/118351
PCT Pub. Date: Jun. 20, 2019

(65) Prior Publication Data
US 2021/0069074 A1   Mar. 11, 2021

Related U.S. Application Data

(60) Provisional application No. 62/598,504, filed on Dec. 14, 2017.

(51) Int. Cl.
| | | |
|---|---|---|
| *A61K 8/28* | (2006.01) |
| *A61K 8/02* | (2006.01) |
| *A61K 8/26* | (2006.01) |
| *A61K 8/44* | (2006.01) |
| *A61Q 5/02* | (2006.01) |
| *A61Q 5/12* | (2006.01) |
| *A61Q 15/00* | (2006.01) |
| *A61Q 19/10* | (2006.01) |

(52) U.S. Cl.
CPC ............ *A61K 8/28* (2013.01); *A61K 8/0275* (2013.01); *A61K 8/26* (2013.01); *A61K 8/44* (2013.01); *A61Q 5/02* (2013.01); *A61Q 5/12* (2013.01); *A61Q 15/00* (2013.01); *A61Q 19/10* (2013.01); *A61K 2800/30* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 3,997,439 A | 12/1976 | Ayukawa | |
| 4,148,812 A * | 4/1979 | Rubino | ............... A61K 8/042 556/27 |
| 5,718,876 A | 2/1998 | Parekh et al. | |
| 7,153,495 B2 | 12/2006 | Parekh et al. | |
| 8,257,689 B2 | 9/2012 | Pan | |
| 8,562,956 B2 | 10/2013 | Pan | |
| 8,603,505 B2 | 12/2013 | Brown et al. | |
| 8,795,641 B2 | 8/2014 | Pan | |
| 9,427,386 B2 | 8/2016 | Pan | |
| 2010/0202993 A1 | 8/2010 | Pan | |
| 2012/0070393 A1* | 3/2012 | Mateu | ................... A61K 8/892 424/68 |
| 2015/0132242 A1 | 5/2015 | Yuan | |

FOREIGN PATENT DOCUMENTS

| | | |
|---|---|---|
| CN | 1279060 | 1/2001 |
| CN | 103705390 | 4/2014 |
| CN | 106687098 | 5/2017 |
| RU | 2333741 | 9/2008 |
| WO | 2009/075678 | 6/2009 |
| WO | 2009/076591 | 6/2009 |
| WO | 2013/158077 | 10/2013 |
| WO | 2016/048340 | 3/2016 |

OTHER PUBLICATIONS

International Search Report and Written Opinion of the International Searching Authority in International Application No. PCT/US2018/064756, dated May 22, 2019.

\* cited by examiner

*Primary Examiner* — Patricia Duffy
*Assistant Examiner* — Garen Gotfredson

(57) ABSTRACT

Described herein are zirconium oxychloride clusters comprising zirconium oxychloride and a basic amino acid. Personal care compositions comprising the same, and methods of making and using the same are also described.

15 Claims, 2 Drawing Sheets

ZIRCONIUM-BASED CLUSTER AS AN ANTIPERSPIRANT AND DEODORANT ACTIVE

BACKGROUND

Antiperspirants are personal hygiene products designed to control sweating and body odor. Antiperspirants contain ingredients that control sweat and body odor safely and effectively. When an antiperspirant is applied to the skin surface, its antiperspirant ingredients, e.g., aluminum salts, dissolve in the sweat or moisture on the skin. The dissolved substance forms a gel, which creates a small temporary plug near the top of the sweat gland, significantly reducing the amount of sweat that is secreted to the skin surface. Antiperspirant actives may also flocculate proteins present in the sweat to form a precipitate which blocks the sweat glands. Although antiperspirants reduce sweating, they do not impact on the natural ability of the body to control its temperature.

It has been known that zirconium salts exhibit effective antiperspirant properties such zirconium compounds include acidic zirconium salts such as zirconium oxychloride or zirconyl chloride, zirconium hydroxychloride, and other halide and sulfate substitutes of the salts. Due to the large charge to size ratio of $Zr^{4+}$, zirconium compounds provide superior sweat reduction efficacy but has a high skin irritation potential. According to FDA antiperspirant over-the-counter monograph, zirconium compounds may be added into polymerized aluminum chloride systems to produce aluminum zirconium chlorohydrates, optionally comprising glycine. The zirconium salts are extremely acidic and irritating to the skin. For example, a solution of zirconium oxychloride which is effective as an antiperspirant has a pH of about 0.8. Thus, zirconium oxychloride alone cannot be used in a topical product due to its extremely low pH value. Moreover, decreasing the acidity of zirconium compounds using weak acids, e.g., organic acids, tends to decrease their antiperspirant efficacy.

There is a need for partially neutralized zirconium compounds that overcome the undesirable effects of highly acidic zirconium compounds and at the same time exhibit desirable properties as antiperspirant/deodorant actives or water treatment agents.

BRIEF SUMMARY

The present invention provides zirconium oxychloride clusters comprising zirconium oxychloride and a basic amino acid e.g., arginine, having a radius of gyration of from 0.5 nm to 50 nm, e.g., from 0.5 nm to 20 nm, from 0.5 nm to 10 nm, from 0.7 nm to 10 nm, from 0.8 nm to 10 nm, from 1 nm to 10 nm, from 0.5 nm to 7 nm, from 0.6 nm to 6 nm, from 0.7 nm to 5 nm, from 0.8 nm to 3 nm, from 0.8 nm to 2.5 nm, or from 1 nm to 2 nm. In some embodiments, the zirconium oxychloride cluster is stable at pH 2-6, 3-5, 3-4, 3.5-4.5, or 4-4.5. In some embodiments, the zirconium oxychloride cluster exhibits a SEC chromatogram having a high peak at 6-8 minutes, 6.5-7.5 minutes, 6.5-7 minutes, or about 6.75 minutes, wherein the SEC chromatogram is obtained under conditions wherein SEC chromatography is carried out using a 10 μm diol-bonded gel filtration column with 20 min run time and 1 mL/min flow rate and the mobile phase of the SEC chromatography consists of deionized water acidified with 1.01% w/w $HNO_3$ to pH 2.3. In some embodiments, the zirconium oxychloride cluster is prepared by a process comprising the steps of: (a) combining a basic amino acid, e.g., arginine, and zirconium oxychloride in aqueous solution; (b) incubating the solution at a temperature higher than 40° C., e.g., from 40° C. to 60° C., from 45° C. to 55° C., or about 50° C.; and (c) cooling the solution, wherein the molar ratio of the basic amino acid to zirconium oxychloride is less than 1.5, e.g., from 0.5 to 1.5, from 0.7 to 1.3, from 0.8 to 1.2, from 0.9 to 1.1, or about 1. In some embodiments, the zirconium oxychloride cluster may be amorphous.

The present invention also provides personal care products, e.g., antiperspirants, comprising the zirconium oxychloride cluster of the invention. In some embodiments, the personal care product further comprises an aluminum containing antiperspirant active. In some embodiments, the personal care product does not contain any aluminum containing antiperspirant active.

The present invention also provides methods of preparing the zirconium oxychloride cluster of the invention, comprising the steps of: (a) combining a basic amino acid, e.g., arginine, and zirconium oxychloride in an aqueous solution; (b) incubating the solution at a temperature higher than 40° C., e.g., from 40° C. to 60° C., from 45° C. to 55° C., or about 50° C.; and (c) cooling the solution, wherein the molar ratio of the basic amino acid to zirconium oxychloride in step (a) is less than 1.5, e.g., from 0.5 to 1.5, from 0.7 to 1.3, from 0.8 to 1.2, from 0.9 to 1.1, or about 1.

The present invention also provides use of the zirconium oxychloride cluster of the invention as an antiperspirant or deodorant active or water treatment agent.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The present invention will become more fully understood from the detailed description and the accompanying drawings.

DETAILED DESCRIPTION

Figure 1:
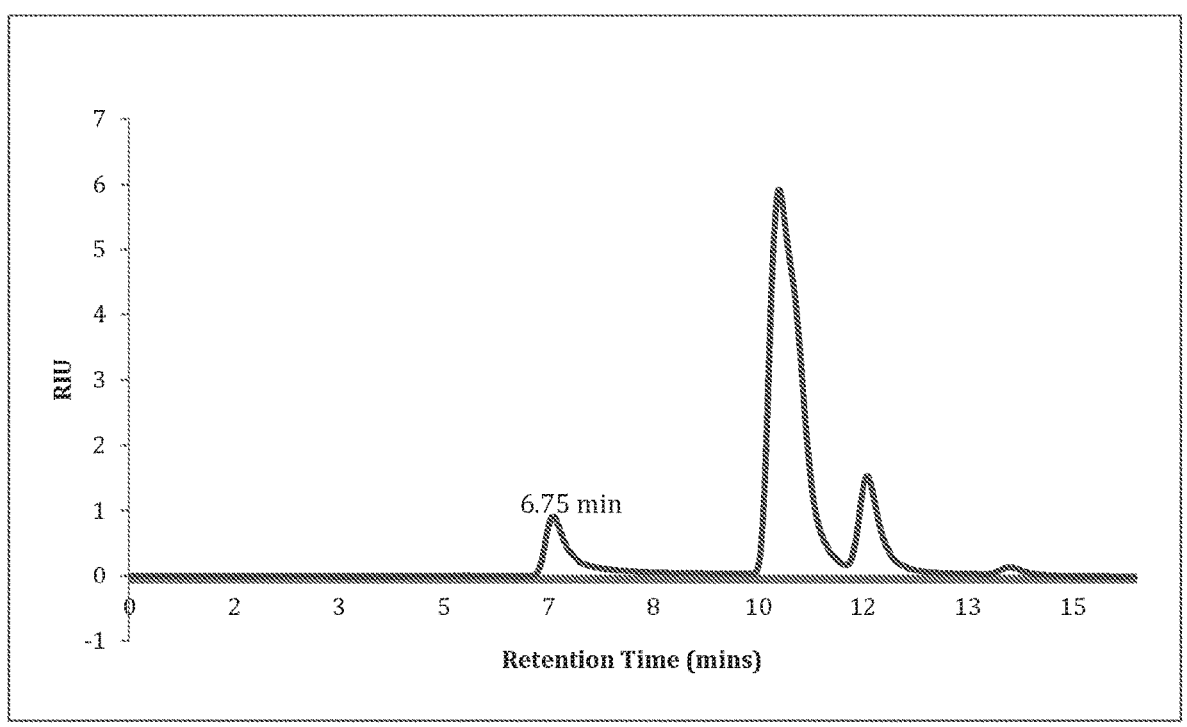
FIG. 1 illustrates a SEC chromatogram of a solution (Arg/Zr 1) in Example 1.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present invention provides a zirconium oxychloride cluster (Cluster 1.0) comprising zirconium oxychloride and a basic amino acid e.g., arginine, having a radius of gyration of from 0.5 nm to 50 nm, e.g., from 0.5 nm to 20 nm, from 0.5 nm to 10 nm, from 0.7 nm to 10 nm, from 0.8 nm to 10 nm, from 1 nm to 10 nm, from 0.5 nm to 7 nm, from 0.6 nm to 6 nm, from 0.7 nm to 5 nm, from 0.8 nm to 3 nm, from 0.8 nm to 2.5 nm, or from 1 nm to 2 nm.

1.1. Cluster 1.0, wherein the radius of gyration of the zirconium oxychloride cluster is measured by small angle X-ray scattering (SAXS).

1.2. Cluster 1.0 or 1.1, wherein the zirconium oxychloride cluster is amorphous.

1.3. Any of the preceding clusters, wherein the zirconium oxychloride cluster is stable at pH 2-6, 3-5, 3-4, 3.5-4.5, or 4-4.5.

1.4. Any of the preceding clusters, wherein the zirconium oxychloride cluster exhibits a SEC chromatogram having a high peak at 6-8 minutes, 6.5-7.5 minutes, 6.5-7 minutes, or about 6.75 minutes; and wherein the SEC chromatogram is obtained under conditions wherein SEC chromatography is carried out using a 10 μm diol-bonded gel filtration column with 20 min run time and 1 mL/min flow rate and the mobile phase of the SEC chromatography consists of deionized water acidified with 1.01% w/w $HNO_3$ to pH 2.3.

1.5. Any of the preceding clusters, wherein the basic amino acid is present in an amount of less than 5%, less than 1%, less than 0.1%, less than 0.01%, less than 0.001%, or less than 0.0001%, by weight of the cluster.

1.6. Any of the preceding clusters, wherein the basic amino acid comprises arginine.

1.7. Cluster 1.6, wherein the basic amino acid comprises L-arginine.

1.8. Any of the preceding cluster prepared by a process comprising the steps of:
(a) combining a basic amino acid and zirconium oxychloride in an aqueous solution;
(b) incubating the solution at a temperature higher than 40° C., e.g., from 40° C. to 60° C., from 45° C. to 55° C., or about 50° C.; and
(c) cooling the solution;
wherein the molar ratio of the basic amino acid to zirconium oxychloride in step (a) is less than 1.5.

1.9. Cluster 1.8, wherein the process further comprises the step of purifying the zirconium oxychloride cluster from the cooled solution.

1.10. Cluster 1.9, wherein the zirconium oxychloride cluster is purified by gel permeation chromatography (GPC).

1.11. Cluster 1.10, wherein the GPC column comprises polyacrylamide beads having a wet bead size of less than 45 μm and a 100-1,800 MW fractionation range.

1.12. Cluster 1.11, wherein the purification comprises loading the cooled solution on the GPC column using a HPLC pump at 0.2 mL/min; and the mobile phase of the GPC chromatography is deionized water.

1.13. Cluster 1.12, wherein GPC fraction is collected in the 1160-1300 minute interval and wherein the 1160-1300 minute interval fraction contains the purified zirconium oxychloride cluster.

1.14. Any of Clusters 1.10-1.13, wherein the process further comprises the step of freeze drying the GPC fraction.

1.15. Any of Clusters 1.8-1.14, wherein the molar ratio of the basic amino acid to zirconium oxychloride in step (a) is from 0.5 to 1.5, from 0.7 to 1.3, from 0.8 to 1.2, from 0.9 to 1.1, or about 1.

1.16. Any of Clusters 1.8-1.15, wherein the basic amino acid in step (a) is arginine.

1.17. Cluster 1.16, wherein the basic amino acid in step (a) is L-arginine.

1.18. Any of Clusters 1.8-1.17, wherein the aqueous solution in step (a) is water.

The present invention also provides a method (Method 2.0) for the preparation of a zirconium oxychloride cluster having a radius of gyration of from 0.5 nm to 50 nm, e.g., from 0.5 nm to 20 nm, from 0.5 nm to 10 nm, from 0.7 nm to 10 nm, from 0.8 nm to 10 nm, from 1 nm to 10 nm, from 0.5 nm to 7 nm, from 0.6 nm to 6 nm, from 0.7 nm to 5 nm, from 0.8 nm to 3 nm, from 0.8 nm to 2.5 nm, or from 1 nm to 2 nm, comprising the steps of:
(a) combining a basic amino acid and zirconium oxychloride in an aqueous solution;
(b) incubating the solution at a temperature higher than 40° C., e.g., from 40° C. to 60° C., from 45° C. to 55° C., or about 50° C.; and
(c) cooling the solution; wherein the molar ratio of the basic amino acid to zirconium oxychloride in step (a) is less than 1.5.

2.1. Method 2.0, wherein the method further comprises the step of purifying the zirconium oxychloride cluster from the cooled solution.

2.2. Method 2.1, wherein the zirconium oxychloride cluster is purified by gel permeation chromatography (GPC).

2.3. Method 2.2, wherein the GPC column comprises polyacrylamide beads having a wet bead size of less than 45 μm and a 100-1,800 MW fractionation range.

2.4. Method 2.3, wherein the purification comprises loading the cooled solution on the GPC column using a HPLC pump at 0.2 mL/min; and the mobile phase of the GPC chromatography is deionized water.

2.5. Method 2.4, wherein GPC fraction is collected in the 1160-1300 minute interval, and wherein the 1160-1300 minute interval fraction contains the purified zirconium oxychloride cluster.

2.6. Any of Methods 2.2-2.5, wherein the method further comprises the step of freeze drying the GPC fraction.

2.7. Any of the preceding methods, wherein the molar ratio of the basic amino acid to zirconium oxychloride in step (a) is from 0.5 to 1.5, from 0.7 to 1.3, from 0.8 to 1.2, or about 1.

2.8. Any of the preceding methods, wherein the basic amino acid in step (a) is arginine.

2.9. Any of the preceding methods, wherein the basic amino acid in step (a) is L-arginine.

2.10. Any of the preceding methods, wherein the aqueous solution in step (a) is water.

2.11. Any of the preceding methods, wherein the radius of gyration of the zirconium oxychloride cluster is measured by small angle X-ray scattering (SAXS).

2.12. Any of the preceding methods, wherein the zirconium oxychloride cluster is amorphous.

2.13. Any of the preceding methods, wherein the zirconium oxychloride cluster is stable at pH 2-6, 3-5, 3-4, 3.5-4.5 or 4-4.5.

2.14. Any of the preceding methods, wherein the zirconium oxychloride cluster exhibits a SEC chromatogram having a high peak at 6-8 minutes, 6.5-7.5 minutes, 6.5-7 minutes, or about 6.75 minutes; and wherein the SEC chromatogram is obtained under conditions wherein SEC chromatography is carried out using a 10 μm diol-bonded gel filtration column with 20 min run time and 1 mL/min flow rate and the mobile phase of the SEC chromatography consists of deionized water acidified with 1.01% w/w $HNO_3$ to pH 2.3.

2.15. Any of the preceding methods, wherein the zirconium oxychloride cluster comprises the basic amino acid.

The term "zirconium oxychloride cluster" herein refers to any zirconium-based cluster comprising zirconium, chloride, oxygen and hydrogen atoms. In some embodiments, the zirconium oxychloride cluster comprises zirconium oxychloride and a basic amino acid. In some embodiments, the zirconium oxychloride cluster may contain a small amount of a basic amino acid. For example, the zirconium oxychloride cluster may contain a basic amino acid in an amount of less than 5%, less than 1%, less than 0.1%, less than 0.01%, less than 0.001%, or less than 0.0001%, by weight of the cluster. The basic amino acid that may be contained in the zirconium oxychloride cluster include, but are not limited to, arginine, lysine, citrullene, ornithine, creatine, histidine, diaminobutanoic acid, diaminopropionic acid, or combinations thereof. In some embodiments, the basic amino acids are selected from arginine, lysine, citrullene, and ornithine. In some embodiments, the basic amino acid comprises arginine, for example, L-arginine.

The zirconium oxychloride cluster of the present invention has a radius of gyration of from 0.5 nm to 50 nm, e.g., from 0.5 nm to 20 nm, from 0.5 nm to 10 nm, from 0.7 nm to 10 nm, from 0.8 nm to 10 nm, from 1 nm to 10 nm, from 0.5 nm to 7 nm, from 0.6 nm to 6 nm, from 0.7 nm to 5 nm, from 0.8 nm to 3 nm, from 0.8 nm to 2.5 nm, or from 1 nm to 2 nm. Radius of gyration (Rg) may be determined by well-known techniques in the art, e.g., small angle X-ray scattering (SAXS) in which X-ray scattering when travelling through the material is measured at small angles. Radius of gyration (Rg) can be calculated from the SAXS data using well-known data processing techniques in the art, e.g., Guinier plot analysis. In some embodiments, radius of gyration (Rg) of the zirconium oxychloride cluster is determined by Small angle X-ray scattering (SAXS) using Guinier plot analysis.

In some embodiments, the zirconium oxychloride cluster of the present invention exhibits a SEC chromatogram having a high peak at 6-8 minutes, 6.5-7.5 minutes, 6.5-7 minutes, or about 6.75 minutes, wherein the SEC chromatogram is obtained under conditions wherein SEC chromatography is carried out using a 10 μm diol-bonded gel filtration column, e.g., PAK 125 column by Waters (Milford, Mass.), with 20 min run time and mL/min flow rate and the mobile phase of the SEC chromatography consists of deionized water acidified with 1.01% w/w $HNO_3$ to pH 2.3.

Size exclusion chromatography (SEC) is a chromatographic method in which molecules in solution are separated by their size, and in some cases molecular weight. SEC provides information on the size of antiperspirant salts in aqueous solutions. For antiperspirant salts including aluminum chlorohydrate, aluminum/zirconium chlorohydrate, and complexes thereof, distinctive peaks have been identified, corresponding to different size populations of the polymer complexes in solution, appearing in a chromatogram as peaks 1, 2, 3, 4 and a peak known as "5,6" (WO2009/075678 and WO2009/076591). Based on the SEC chromatogram, it is predicted that the zirconium oxychloride cluster of the invention has a particle size on the order of nanometer. A peak in this region of retention time is commonly present in various non-activated antiperspirant active salts, but seldom observed in aluminum-free zirconium compounds. In this disclosure, the zirconium oxychloride cluster of the invention exhibiting a SEC chromatogram having a high peak at 6-8 minutes, e.g., about 6.75 minutes is also referred to as "Zr peak 1". The SEC technique is explained fully in WO 2013/158077 and U.S. 2015/0132242, each of which is incorporated by reference herein in its entirety for all purposes.

In some embodiments, the zirconium oxychloride cluster of the present invention is amorphous.

In some embodiments, the zirconium oxychloride cluster of the invention is stable at pH 2-6, 3-5, 3-4, 3.5-4.5 or 4-4.5, in solution, e.g., in aqueous solution. In this disclosure, the zirconium oxychloride cluster is stable means that the cluster does not form a gel or precipitate.

In some embodiments, the zirconium oxychloride cluster may be prepared by a process comprising the steps of: (a) combining a basic amino acid, e.g., arginine, and zirconium oxychloride ($ZrOCl_2.8H_2O$, MW 322.25) in an aqueous solution; (b) incubating the solution at a temperature higher than 40° C. e.g., from 40° C. to 60° C., from 45° C. to 55° C., or about 50° C.; and (c) cooling the solution, wherein the molar ratio of the basic amino acid to zirconium oxychloride is less than 1.5. The solution may be incubated at a temperature higher than 40° C., e.g., from 40° C. to 60° C., from 45° C. to 55° C., or about 50° C. for more than 1 hour, e.g., more than 6 hour, more than 12 hour, more than 1 day, from 1 hour to 2 day, from 6 hour to 2 day, from 12 hour to 2 day, or about 1 day. The term "zirconium oxychloride" herein refers to zirconium oxychloride octahydrate ($ZrOCl_2.8H_2O$, MW 322.25). In the process, low molar ratio of the basic amino acid to zirconium oxychloride in step (a) is critical to obtain stable zirconium oxychloride clusters. When the molar ratio of the basic amino acid to zirconium oxychloride is high, e.g., more than 2, solid gel forms during the process. However, when the molar ratio of the basic amino acid to zirconium oxychloride is low, e.g., less than 1.5, from 0.5 to 1.5, from 0.8 to 1.2, or about 1, the produced zirconium oxychloride clusters are stable in terms of gelation and flocculation. In some embodiments, the molar ratio of the basic amino acid to zirconium oxychloride in step (a) is from 0.5 to 1.5, from 0.7 to 1.3, from 0.8 to 1.2, or about 1. In some embodiments, the aqueous solution in step (a) is water.

In some embodiments, the basic amino acids which can be used in the process of preparing the zirconium oxychloride cluster of the invention include not only naturally occurring basic amino acids, such as arginine, lysine, and histidine, but also any basic amino acids having a carboxyl group and an amino group in the molecule. Accordingly, basic amino acids include, but are not limited to, arginine, lysine, citrullene, ornithine, creatine, histidine, diaminobutanoic acid, diaminopropionic acid, or combinations thereof. In some embodiments, the basic amino acids are selected from arginine, lysine, citrullene, and ornithine. In some embodiments, the basic amino acid is arginine, for example, L-arginine.

In some embodiments, the prepared zirconium oxychloride cluster may be further purified. For example, zirconium oxychloride cluster may be purified by gel permeation chromatography (GPC). Gel permeation chromatography (GPC) is a type of size exclusion chromatography (SEC) that separates molecules on the base of size. In some embodiments, the purification comprises loading the solution containing zirconium oxychloride clusters on the GPC column comprising polyacrylamide beads having a wet bead size of less than 45 μm and a 100-1,800 MW fractionation range, e.g., Bio-Rad P2 gel with 5 μm particle size, using a HPLC pump at 0.2 mL/min; and the mobile phase of the GPC chromatography is deionized water. GPC fraction is collected in the 1160-1300 minute interval and the 1160-1300 minute interval fraction contains the purified zirconium cluster. In some embodiments, the GPC fraction may be freeze dried to obtain purified powder.

Although zirconium oxychloride exhibits effective antiperspirant properties, zirconium oxychloride alone cannot be used in a topical product due to its extremely low pH value (less than pH 2). It has been found that the zirconium oxychloride cluster of the present invention is stable at higher pH. Thus, the zirconium oxychloride cluster can overcome the undesirable effects of highly acidic zirconium compounds. Moreover, it has been found that the zirconium oxychloride cluster of the invention forms a precipitate in presence of proteins such as bovine serum albumin (BSA), suggesting that the zirconium oxychloride cluster can flocculate proteins present in the sweat to enhance the formation of plugs in the sweat ducts. Thus, the zirconium oxychloride cluster of the invention can be used as an antiperspirant and deodorant active.

The present invention also provides personal care compositions, e.g., antiperspirants, comprising a zirconium oxychloride cluster according to any of Clusters 1.0-1.18. The personal care composition may be any composition in which it is desired to include an antiperspirant and deodorant active for application to the skin. Examples of such compositions include, but are not limited to, antiperspirants, deodorants, body washes, shower gels, bar soaps, shampoo, hair conditioners, cosmetics, etc.

In some embodiments, the zirconium oxychloride cluster used in the personal care composition may be prepared by a method according to any of Methods 2.0-2.15. The zirconium oxychloride cluster used in the personal care composition may be a purified or unpurified form.

The personal care composition contains a carrier. For antiperspirant/deodorant compositions, the carrier can be any carrier that is used for antiperspirants/deodorants. The carrier can be in the form of a stick, a gel, a roll-on, or an aerosol. For stick formulations, the carrier may include oils and/or silicones and gelling agents.

The antiperspirant compositions can be formulated into topical antiperspirant and/or deodorant formulations suitable for application to skin, illustratively a stick, a gel, a cream, a roll-on, a soft solid, a powder, a liquid, an emulsion, a suspension, a dispersion or a spray. The composition can comprise a single phase or can be a multi-phase system, for example a system comprising a polar phase and an oil phase, optionally in the form of a stable emulsion. The composition can be liquid, semi-solid or solid. The antiperspirant and/or deodorant formulation can be provided in any suitable container such as an aerosol can, tube or container with a porous cap, roll-on container, bottle, container with an open end, etc.

Optional ingredients that can be included in an antiperspirant and/or deodorant formulation include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the zirconium oxychloride cluster can be included, for example an odor reducing agent such as a sulfur precipitating agent, e.g., copper gluconate, zinc gluconate, zinc citrate, etc.

In some embodiments, the personal care composition may further comprise additional antiperspirant actives. The additional active antiperspirant ingredient may be selected from aluminum salts, zirconium salts and zinc salts. In some embodiment, the personal care composition may comprise an aluminum containing antiperspirant active. Any of the known aluminum containing antiperspirant active materials can be utilized in the composition. Aluminum containing antiperspirant actives include, but are not limited to, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum, sesquichlorohydrate polyethylene glycol, aluminum sesquichlorohydrate propylene glycol.

In some embodiments, the personal care composition does not contain any other antiperspirant active. In some embodiment, the personal care composition does not contain any aluminum containing antiperspirant active.

In some embodiments, the personal care composition may include any known deodorant active. Examples of deodorant actives include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammomium bromide, cetyl pyridinium chloride, farnesol (3,7, 11-trimethyl-2,6,10-dodecatrien-1-ol), N-(4-chlorophenyl)-N'-(3,4-dichlorophenyl)urea (Triclocarban), silver halides, octoxyglycerin (Sensiva™ SC 50) and various zinc salts (for example, zinc ricinoleate), bactericides, and/or bacteriostats. The deodorant active can be included in the composition in an amount of 0-5%, or 0.01-1% by weight, of the total weight of the composition. Triclosan can be included in an amount of 0.05% to 0.5% by weight, of the total weight of the composition.

In some embodiments, gelling agents may be included in the personal care composition. Examples of gelling agents include, but are not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, or other cosmetically acceptable materials, which are solid or semi-solid at room temperature and provide a consistency suitable for application to the skin.

In some embodiments, fragrance may be included in the personal care composition. Any fragrance suitable for personal care use may be incorporated into the personal care composition of the present invention. Fragrances tend to be relatively volatile aroma compounds which are capable of entering the gas phase at skin surface temperature.

The personal care compositions of the present invention may be manufactured using methods known in the art. Typically, the ingredients are combined and optionally heated where components need to be melted. The components are mixed. Desirably, volatile materials such as fragrant materials are incorporated in the composition in the latter stages of a mixing cycle in order to avoid volatilization thereof. After mixing, the composition may be poured directly into the dispensers and the container capped to preserve the product until use.

The present invention also provides use of the zirconium oxychloride cluster as described herein as an antiperspirant or deodorant active or water treatment agent.

EXAMPLES

Example 1: Preparation of Zirconium Oxychloride Clusters

Samples were prepared according to Table 1. Water was added to zirconium oxychloride ($ZrOCl_2 \cdot 8H_2O$, MW 322.25) in a glass jar to yield a clear solution containing 1% zirconium oxychloride. Under stirring, L-arginine was slowly added to prevent clumping of arginine as well as large fluctuations in localized pH values. The molar ratio of arginine to zirconium oxychloride was 0.5:1, 1:1, 2:1, 3:1, and 4:1, as shown in Table 1. The solutions were incubated for 1 day at 50° C. Then the solutions were cooled to room temperature. Solid gel was formed in samples with the molar ratio of arginine to zirconium oxychloride of 2-4. However, at the molar ratio of arginine to zirconium oxychloride to 0, 0.5 and 1, the samples were stable in terms of gelation and flocculation with pH of 1.39, 1.73, and 2.59, respectively.

TABLE 1

1% zirconium oxychloride with varied arginine

| | Calculated | | | | Experimental | | | | |
|---|---|---|---|---|---|---|---|---|---|
| Sample | Arg/Zr mol | Zr g | Arg g | Total g | Arg/Zr mol | Zr g | Arg g | Total g | pH |
| Zr | 0 | 0.3533 | 0 | 10 | 0 | 0.3533 | 0 | 9.9928 | 1.39 clear |
| Arg/Zr 0.5 | 0.5 | 0.3533 | 0.0955 | 10 | 0.49 | 0.3531 | 0.0944 | 9.9955 | 1.73 clear |
| Arg/Zr 1 | 1 | 0.3533 | 0.1910 | 10 | 1.00 | 0.3534 | 0.1912 | 10.0117 | 2.59 clear |
| Arg/Zr 2 | 2 | 0.3533 | 0.3819 | 10 | 2.00 | 0.3540 | 0.3818 | 10.0140 | gel |
| Arg/Zr 3 | 3 | 0.3533 | 0.5729 | 10 | 2.99 | 0.3541 | 0.5729 | 9.9993 | gel |
| Arg/Zr 4 | 4 | 0.3533 | 0.7638 | 10 | 4.01 | 0.3526 | 0.7639 | 9.9970 | gel |

SEC-RI analysis was carried out on the sample with Arg/Zr molar ratio of 1. SEC was equipped with a differential refractive index (dRI) detector. Separation was carried out using a Protein Pak 125 column by Waters (Milford, Mass.) with 20 min run time and 1 mL/min flow rate. The mobile phase consisted of deionized water acidified with 1.01% w/w $HNO_3$ to pH 2.3. SEC chromatogram exhibited a peak at 6.75 minute (FIG. 1). A peak in this region of retention time is commonly present in various non-activated antiperspirant active salts, but seldom observed in aluminum-free zirconium compounds. Based on the SEC data, it was predicted that the prepared zirconium compound is a zirconium-based cluster (zirconium oxychloride cluster) with a particle size of the order of nanometer. Synchrotron-small-angle X-ray scattering (SAXS) analysis was further carried out to determine the radius of gyration of the zirconium oxychloride cluster. The distribution of radius of gyration was extracted from the SAXS data using Guinier plot analysis. There existed a main peak near 1.1 nm and a small shoulder peak near 2 nm. The SAXS analysis showed that radius of gyration of most zirconium oxychloride clusters is within 0.8 nm-3 nm.

Example 2: Purification of Zirconium Oxychloride Clusters

A 100 g batch was prepared according to Table 2. 1% w/w zirconium oxychloride ($ZrOCl_2 \cdot 8H_2O$, MW 322.25) and arginine were mixed in aqueous solution with the molar ratio of arginine to zirconium oxychloride of 1:1.

TABLE 2

1% zirconium oxy chloride with arginine (1:1 ratio) (100 g batch)

| | Calculated | | | | Experimental | | | | |
|---|---|---|---|---|---|---|---|---|---|
| Sample | Arg/Zr mol | Zr g | Arg g | Total g | Arg/Zr mol | Zr g | Arg g | Total g | pH |
| Arg/Zr 1 | 1 | 3.5325 | 1.9096 | 100 | 1 | 3.53 | 1.91 | 100.06 | 2.31 |

Figure 2:
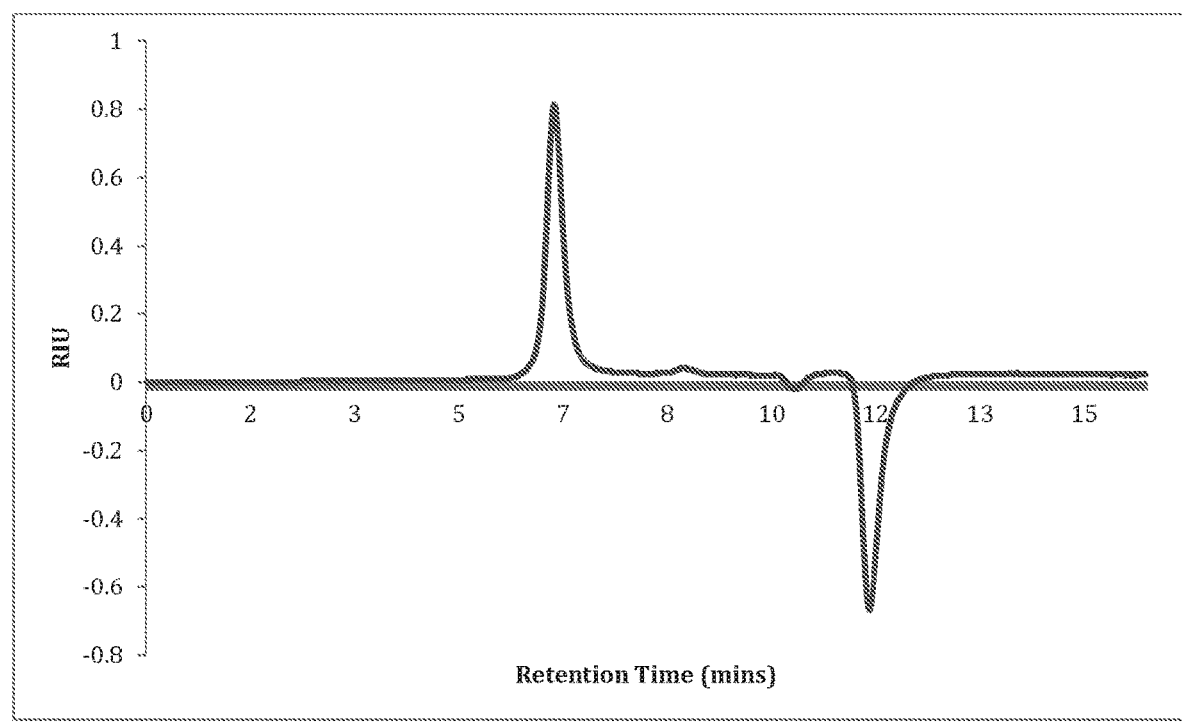
FIG. 2 illustrates a SEC chromatogram of the GPC fraction 1160-1300 min in Example 2.

The zirconium oxychloride cluster was prepared as described in Example 1. The prepared zirconium oxychloride cluster was purified by gel permeability chromatograph (GPC). GPC column was prepared using Bio-Rad P2 gel with 5 μm particle size. Approximately 10 mL of prepared solution was filtered (0.45 μm) and loaded on the column using a HPLC pump at 0.2 mL/min. The mobile phase of the GPC chromatography was deionized water. Elution fractions were collected in intervals and monitored using SEC-RI. The first species to elute exhibited a peak of SEC at 6.75 minute indicative of the zirconium oxychloride clusters. Highest concentration of the zirconium oxychloride clusters was observed in the 1160-1300 min GPC fraction. SEC-RI chromatogram of GPC fraction 1160-1300 min is shown in FIG. 2. The pH of the GPC fraction (1160-1300 min) was 4.5. The zirconium oxychloride cluster in this GPC fraction was stable in terms of gelation and flocculation. 10 g of this fraction was freeze dried to obtain purified powder for subsequent PXRD analysis. PXRD (Powder X-Ray Diffraction) analysis revealed non-crystalline packing arrangements, indicating the zirconium oxychloride cluster is amorphous.

Example 3: Flocculation

One of mechanisms of antiperspirant action is that antiperspirants combine with proteins present in the sweat to form a precipitate which blocks the sweat glands. To test whether the zirconium oxychloride cluster, also referred to as Zr Peak 1 herein, can precipitate in a sweat environment and thus behave as an antiperspirant, bovine serum albumin (BSA) was used as a model protein to simulate proteins found on skin surface and sweat environments. Zirconium oxychloride cluster was prepared as described in Example 1. Specifically, 94.6 g of water was added to 3.5377 g of zirconium oxychloride ($ZrOCl_2 \cdot 8H_2O$) in a glass jar to yield a clear solution. Under stirring, 1.9104 g of L-arginine was slowly added to prevent clumping of arginine as well as large fluctuations in localized pH values. This clear solution was heated at 50° C. for 24 hours. Then the solution was cooled to room temperature. After preparation of the Zr Peak 1 solution, 1% w/w solution of BSA was freshly prepared and sonicated until the solution becomes clear. 1% BSA solution was subsequently added dropwise to the Zr Peak 1 solution, at which point precipitation was observed. This result shows that the zirconium oxychloride cluster (Zr Peak 1) can form a precipitate in presence of proteins such as BSA, suggesting that the zirconium oxychloride cluster can flocculate proteins present in the sweat to enhance the formation of plugs in the sweat ducts. This result suggests that the zirconium oxychloride cluster can be used as an antiperspirant and deodorant active.

While the disclosure has been described with respect to specific examples including presently preferred modes of carrying out the disclosure, those skilled in the art will appreciate that there are numerous variations and permutations of the above described systems and techniques. It is to be understood that other embodiments may be utilized and structural and functional modifications may be made without departing from the scope of the present disclosure. Thus, the scope of the disclosure should be construed broadly as set forth in the appended claims.

What is claimed is:

1. A personal care composition comprising a zirconium oxychloride cluster comprising:
    a. zirconium oxychloride; and
    b. a basic amino acid, wherein the basic amino acid is arginie;
    wherein the cluster has a radius of gyration of from 0.5 nm to 50 nm,
    wherein the cluster is aluminum-free,
    wherein molar ration of the basic amino acid to zirconium oxychloride is from 0.5:1 to 1:1, and
    wherein the personal care composition is not in gel form.

2. The personal care composition of claim 1, wherein the zirconium oxychloride cluster has a radius of gyration of from 0.5 nm to 20 nm, from 0.5 nm to 10 nm, from 0.7 nm to 10 nm, from 0.8 nm to 10 nm, from 1 nm to 10 nm, from 0.5 nm to 7 nm, from 0.6 nm to 6 nm, from 0.7 nm to 5 nm, from 0.8 nm to 3 nm, from 0.8 nm to 2.5 nm, or from 1 nm to 2 nm.

3. The personal care composition of claim 1, wherein the zirconium oxychloride cluster is stable at pH 2-6, 3-5, 3-4, 3.5-4.5 or 4-4.5.

4. The personal care composition of claim 1, wherein the zirconium oxychloride cluster exhibits a size exclusion chromatography (SEC) chromatogram having a high peak at 6-8 minutes; wherein the SEC chromatogram is obtained under conditions wherein SEC chromatography is carried out using a 101.tm diol-bonded gel filtration column with 20 min run time and 1 mL/min flow rate and the mobile phase of the SEC chromatography consists of deionized water acidified with 1.01% w/w $HNO_3$ to pH 2.3.

5. The personal care composition of claim 1 prepared by a process comprising the steps of:
    (a) combining a basic amino acid and zirconium oxychloride in an aqueous solution;
    (b) incubating the solution at a temperature higher than 40° C.; and
    (c) cooling the solution;
    wherein the molar ratio of the basic amino acid to zirconium oxychloride in step (a) is from 0.5:1 to 1:1.

6. The personal care composition of claim 5, wherein the molar ratio of the basic amino acid to zirconium oxychloride in step (a) is 0.5:1 to 1:1.

7. The personal care composition of claim 5, wherein the arginine is L-arginine, and the cluster is prepared by
    (a) adding L-arginine under stirring to a clear solution containing 1% zirconium oxychloride, wherein the molar ratio of arginine to zirconium oxychloride is from 0.5:1 to 1:1.
    (b) incubating the solution for 1 day at 50° C.; an
    (c) cooling the solution down to room temperature;
    wherein said molar ratios of from 0.5:1 to 1:1 demonstrates better stability in terms of gelation and flocculation under pH of 1.39, 1.73, or 2.59, than molar ratios of 2:1, 3:1 and 4:1.

8. The personal care composition of claim 5, wherein the process further comprises the step of purifying the zirconium oxychloride cluster from the cooled solution.

9. The personal care composition of claim 8, wherein the zirconium oxychloride cluster is purified by gel permeation chromatography (GPC).

10. The personal care composition of claim 9, wherein the GPC column comprises polyacrylamide beads having a wet bead size of less than 45μm and a 100-1,800 MW fractionation range.

11. The personal care composition of claim 10, wherein the purification comprises loading the cooled solution on the GPC column using a HPLC pump at 0.2 mL/min; and the mobile phase of the GPC chromatography is deionized water.

12. The personal care composition of claim 11, wherein GPC fraction is collected in the 1160-1300 minute interval and wherein the 1160-1300 minute interval fraction contains the purified zirconium cluster.

13. The personal care composition of claim 1, wherein the personal care composition comprises an aluminum containing antiperspirant active.

14. The personal care composition of claim 1, wherein the personal care composition does not contain any aluminum containing antiperspirant active.

15. The personal care composition of claim 1, wherein the personal care composition is selected from an antiperspirant, a deodorant, a body wash, a shower gel, a bar soap, a shampoo, a hair conditioner, and a cosmetic.

* * * * *